United States Patent [19]
Dubief et al.

[11] Patent Number: 5,240,695
[45] Date of Patent: Aug. 31, 1993

[54] USE OF 2-HYDROXY-4-METHOXYBENZOPHE-NONE-5-SULPHONIC ACID OR ITS SALTS FOR PROTECTING THE HAIR AGAINST ENVIRONMENTAL ATTACKING AGENTS, AND ESPECIALLY AGAINST LIGHT AND PROCESS FOR PROTECTING THE HAIR USING THE COMPOUND

[75] Inventors: Claude Dubief, Le Chesnay; Jean F. Grollier, Paris, both of France

[73] Assignee: L'Oreal, Paris, France

[21] Appl. No.: 962,676

[22] Filed: Oct. 19, 1992

Related U.S. Application Data

[63] Continuation of Ser. No. 308,727, Feb. 10, 1989, abandoned.

[30] Foreign Application Priority Data

Feb. 11, 1988 [LU] Luxembourg .......................... 87130

[51] Int. Cl.$^5$ .......................... A61K 7/08; A61K 7/06; A61K 7/075
[52] U.S. Cl. .......................... 424/47; 424/70; 424/78.03; 424/78.31
[58] Field of Search .................. 424/78.03, 78.01, 70, 424/47

[56] References Cited

U.S. PATENT DOCUMENTS 3,670,074  6/1972  Doner .......................... 424/60
4,726,945  2/1988  Patel et al. ..................... 424/70
4,804,531  2/1989  Grollier ......................... 424/60

FOREIGN PATENT DOCUMENTS 0193932  9/1986  European Pat. Off. .
2046818  9/1970  Fed. Rep. of Germany .
2509989  7/1981  France .

OTHER PUBLICATIONS

European Search Report, Aug. 1988.

Primary Examiner—Howard E. Schain
Attorney, Agent, or Firm—Cushman, Darby & Cushman

[57] ABSTRACT

Use of 2-hydroxy-4-methoxybenzophenone-5-sulphonic acid or its salts of protecting the hair against environmental attacking agents, and especially against light, and process for protecting the hair using this compound.

Use for preserving the mechanical properties of the hair from degradation by environmental attacking agents, and especially by light, of at least 0.3% by weight of 2-hydroxy-4-methoxybenzophenone-5-sulphonic acid, in a cosmetically acceptable aqueous, alcoholic or aqueous-alcoholic vehicle.

The acid is optionally salified with a metal hydroxide, ammonia solution or an amine.

The invention also relates to a process for protecting the keratin of the hair against light, consisting in applying on the hair at least 30 mg/g of hair of a cosmetic composition containing at least 0.3% by weight of 2-hydroxy-4-methoxybenzophenone-5-sulphonic acid.

14 Claims, No Drawings

USE OF 2-HYDROXY-4-METHOXYBENZOPHENONE-5-SULPHONIC ACID OR ITS SALTS FOR PROTECTING THE HAIR AGAINST ENVIRONMENTAL ATTACKING AGENTS, AND ESPECIALLY AGAINST LIGHT AND PROCESS FOR PROTECTING THE HAIR USING THE COMPOUND

This is a continuation of application No. 07/108,727, filed Feb. 10, 1989, now abandoned.

Use of 2-hydroxy-4-methoxybenzophenone-5-sulphonic acid or its salts for protecting the hair against environmental attacking agents, and especially against light, and process for protecting the hair using this compound.

The present invention relates to the use of 2-hydroxy-4-methoxybenzophenone-5-sulphonic acid and its salts as agents for protecting the keratin of the hair against environmental attacking agents, and especially against light, and a process for protecting the hair against environmental attacking agents, and especially against light.

It has been known for a long time that light attacks the keratin of the hair. Many publications disclose that natural light destroys some amino acids of the hair and that, by degrading the hair fibre, it reduces some of the mechanical properties of the latter; a reduction of mechanical properties is understood chiefly to mean reduction in the 15% extension level.

The 15% extension level is the weight which must be applied to a wet hair of a given length in order to elongate it by 15%. The higher the weight the more elastic and resistant the hair.

To combat attack of the keratin of the hair by light, the use of substances capable of screening out light radiation has already been proposed. In particular, screening agents well known in the art have been tried, such as benzophenone derivatives, for example 2-hydroxy-4-methoxybenzophenone and 2,2'-dihydroxy-4,4'-dimethoxy-5,5'-disulphobenzophenone disodium salt, or alternatively dibenzoylmethane derivatives, for example 4-tert-butyl-4'-methoxydibenzoylmethane, or p-aminobenzoic acid and its derivatives such as 2-ethylhexyl p-dimethylaminobenzoate and (4'-dimethylaminobenzoyloxyethyl)dimethyl($C_{15}$-$C_{18}$alkyl) ammonium tosylate (ESCALOL 537 Q), cinnamates such as 2-ethylhexyl p-methoxycinnamate or alternatively 2-phenylbenzimidazole-5-sulphonic acid.

However, these screening substances have not proved effective for preserving the mechanical properties of the hair, namely their elasticity, against the deleterious effects of light.

It has, on the contrary, become apparent that their presence in some cosmetic compositions could even enhance the degradation of the mechanical properties, in particular the reduction in the 15% extension level.

The applicants have now discovered, altogether surprisingly, that 2-hydroxy-4-methoxybenzophenone-5-sulphonic acid, sold, for example, under the name "UVINUL MS40" by BASF, or its salts, could preserve the mechanical properties of the hair from degradation by light. This property could be demonstrated by exposure in natural light (sunny environment) and in artificial light (xenon emitter of an accelerated aging apparatus of the SUNTEST HANAU).

The subject of the present invention is hence the use of 2-hydroxy-4-methoxy-benzophenone-5-sulphonic acid or its salts as agents for protecting the mechanical properties of the hair, and chiefly the 15% extension level in the wet state, against the degradation caused by environmental attacking agents, and especially by light.

Salts of the abovementioned sulphonic acid are understood, more especially, to mean metal salts such as the alkali metal or alkaline-earth metal salts, and ammonium and amine salts.

According to the present invention, 2-hydroxy-4-methoxybenzophenone-5-sulphonic acid or its salts is/are used for preserving the mechanical properties of the hair from attack by light, in quantities at least equal to 0.3% by weight of free acid, and preferably between 0.3 and 9% by weight of free acid, in a cosmetically acceptable aqueous, alcoholic or aqueous-alcoholic vehicle. The minimal concentration of 0.3% corresponds to a molar concentration per 100 g of composition of approximately 1 millimole of acid, which can be used in free form or salified with a metal hydroxide, ammonia solution or an amine.

2-Hydroxy-4-methoxybenzophenone-5-sulphonic acid or its salts according to the invention may be used for protecting natural or sensitized hair. "Sensitized hair" is understood to mean hair which has undergone a permanent-waving, dyeing or bleaching treatment.

The cosmetic compositions for hair, used according to the invention for protecting it against degradation by light and containing, by way of active compound, 2-hydroxy-4-methoxybenzophenone-5-sulphonic acid or its salts, may be presented in the form of thickened or unthickened aqueous, alcoholic or aqueousalcoholic solutions (the alcohol being, more often than not, a lower alkanol such as ethanol or isopropanol), of gels, of aerosol foams or of sprays, and can contain the adjuvants customarily used in hair-care compositions and which are suitable for the application envisaged.

These compositions can be or need not be followed by a rinsing, and can constitute shampoos, aftershampoos, products to be rinsed for application before or after shampooing, before or after dyeing or bleaching, before or after permanent-waving or straightening, nonrinsed compositions such as lotions, gels, sprays or foams for setting or blow-drying, lacquers or sprays for maintaining the hair style and restructuring compositions.

When the cosmetic compositions used according to the invention constitute compositions not followed by a rinsing, the 2-hydroxy-4-methoxybenzophenone-5-sulphonic acid or its salts, as an active agent preserving the mechanical properties of the hair against light, is/are present in the proportion of 0.3 to 5% by weight of free acid relative to the total weight of the composition, and preferably in the proportion of 0.3 to 3.5% by weight of free acid.

When the cosmetic compositions used according to the invention constitute compositions followed by a rinsing, the 2-hydroxy-4-methoxybenzophenone-5-sulphonic acid or its salts is/are present in the proportion of 0.5 to 9% by weight of free acid, and preferably 0.5 to 6% by weight of free acid, relative to the total weight of the composition.

The cosmetic compositions for hair according to the invention have a pH of between 2 and 9, and preferably between 4 and 8.

The cosmetic compositions used according to the invention can also contain cosmetic agents which are well known in the art, with the proviso that they do not themselves degrade the mechanical properties of the keratin of the hair.

The adjuvants or cosmetic agents generally present in the cosmetic compositions used according to the invention are, for example, cationic, anionic, amphoteric or nonionic surfactants or mixtures thereof, thickeners, anionic, nonionic, amphoteric, cationic polymers or mixtures thereof, emollients, preservatives, foaming agents, foam stabilizers, electrolytes, pH-regulating agents, anti-grease agents, sequestering agents, perfumes, colorings, propellants and organic solvents.

The cationic, anionic, nonionic and amphoteric surfactants, or mixtures thereof, are generally used in proportions of 0.1 to 50% by weight, and preferably 0.5 to 30% by weight, relative to the total weight of the composition.

When the cosmetic compositions for hair used according to the invention constitute shampoos, the latter are essentially characterized in that they contain, apart from the sulphonic acid or its salts defined above, at least one anionic, nonionic, cationic or amphoteric surfactant, or a mixture of such surfactants, in an aqueous medium. Shampoos can also contain different adjuvants such as colorings, preservatives, thickening agents, foam-stabilizing agents, synergists, emollient agents, electrolytes, sequestering agents, one or more cosmetic resins, perfumes and natural oils, as well as any other adjuvant customarily used in a shampoo. In these shampoos, the concentration of surfactant is generally between 2 and 50% by weight. Their pH is generally between 3 and 9.

When the compositions used according to the invention constitute non-rinsed compositions—lotion, gel, foam, spray or lacquer for blow-drying, for setting, for styling or treating the hair—they generally comprise, in an aqueous, alcoholic or aqueous-alcoholic medium, in addition to the sulphonic acid or its salts, at least one cationic, anionic, nonionic or amphoteric polymer, or a mixture of such polymers, in quantities generally of between 0.1 and 10%, and preferably between 0.1 and 3%, by weight, and optionally anti-foaming agents.

When the hair-care compositions according to the invention constitute rinsed lotions, also known as a "rinse", they are applied before or after dyeing or bleaching, before or after permanent-waving, before or after shampooing or between two stages of shampooing, and then rinsed after an exposure time.

These compositions can be aqueous or aqueous-alcoholic solutions optionally comprising surfactants; they can also be gels. These compositions can also be pressurized as an aerosol in the form of sprays or foams.

In these rinsed compositions, the concentration of surfactant agents can vary between 0.1 and 10%, and preferably between 0.5 and 7%, by weight. They can also contain nonionic, cationic, anionic or amphoteric polymers, or mixtures thereof.

When the hair-care compositions are presented in the form of gels, to be rinsed or otherwise, they contain thickeners in the presence or absence of solvents.

The thickeners can be sodium alginate, gum arabic or xanthan gum, or cellulose derivatives such as methylcellulose, hydroxymethylcellulose, hydroxyethylcellulose, hydroxypropylcellulose or carboxymethylcellulose, or carboxylic polymers such as "Carbopols". It is also possible to obtain a thickening of the lotions by mixing polyethylene glycol and polyethylene glycol stearate or distearate, or by a mixture of amides and phosphoric esters. The concentration of thickener can vary from 0.1 to 30%, and preferably from 0.2 to 15%, by weight relative to the total weight of the composition.

It is also possible to use a thickening agent which results from the ionic interaction of a cationic polymer comprising a copolymer of cellulose or of a cellulose derivative, these copolymers being grafted with a water-soluble quaternary ammonium monomer salt (and sold under the names "CELQUAT H 100" or "CELQUAT L 200"), and a carboxylic anionic polymer having an absolute capillary viscosity in dimethylformamide or methanol at a concentration of 5% and at 30° C. of not more than $30 \times 10^{-3}$: Pa.s.

This thickener is described in Patent Application FR 2,598,611.

When the hair-care compositions are presented in the form of foams, to be rinsed or otherwise, they contain a foaming agent in an aqueous or aqueous-alcoholic medium, in the presence of a propellant gas.

As a foaming agent, it is possible to use anionic, nonionic, cationic or amphoteric surfactants, or mixtures thereof, nonionic, anionic or cationic polymers, or mixtures thereof, or polyvinyl alcohol derived from hydrolyzed polyvinyl acetate in which the degree of hydrolysis is not more than 97%, as described in Patent Application FR 2,598,613.

To form a foam, it is preferable to use a combination of cationic polymer and anionic polymer, at least one of the two polymers being foaming in aqueous solution. Such combinations ar described in Patent FR 2,505,348.

The propellant gases used for pressurizing these compositions intended for forming foams are present in proportions not exceeding 25%, and preferably 15%, relative to the total weight of the composition. By way of a propellant gas, it is possible to use carbon dioxide, nitrogen, nitrous oxide, volatile hydrocarbons such as butane, isobutane, propane and mixtures thereof, and non-hydrolysable chlorinated and/or fluorinate hydrocarbons such as those sold under the names "FREON" or "DYMEL" by the Company DU PONT de NEMOURS.

When the composition is presented in the form of a spray or lacquer, it contains a film-forming resin in an alcoholic or aqueous-alcoholic medium, optionally in the presence of a propellant gas. As a film-forming resin, it is preferable to use an anionic polymer containing units of acrylic or methacrylic acid, of crotonic acid or of unsaturated $\alpha,\beta$-dicarboxylic acids.

The propellant agents used in these formulations in the form of lacquers may be chosen from volatile hydrocarbons such as n-butane, propane, isobutane or mixtures thereof, or a mixture of these hydrocarbons with chlorinated and/or fluorinated hydrocarbons such as the compounds sold under the name "FREON" or "DYMEL" by the Company DU PONT de NEMOURS, and more especially fluorochlorohydrocarbons such as monofluorotrichloromethane, difluorodichloromethane, tetrafluorodichloroethane or mixtures of the latter.

They may also be chosen from the chlorinated and/or fluorinated hydrocarbons described above and mixtures thereof, dimethyl ether, carbon dioxide or nitrous oxide.

The propellant phase in these lacquer compositions represents 30 to 80% of the total weight of the pressurized composition.

When the hair-care compositions of the invention constitute restructuring lotions, they contain products strengthening the keratin chain of the hair. To this class of product belong the methylol derivatives such a those described in French Patents Nos. 1,527,085 and 1,519 979.

The present invention also relates to a process for protecting the keratin of the hair against environmental attacking agents, and especially against light, consisting in applying on the hair at least 30 mg/g of hair of a cosmetic composition containing at least 0.3% by weight of 2-hydroxy-4-methoxybenzophenone-5-sulphonic acid, optionally salified, in a cosmetically acceptable aqueous, alcoholic or aqueous-alcoholic vehicle.

According to a preferred embodiment, the cosmetic composition contains 0.3 to 9% by weight of 2-hydroxy-4-methoxybenzophenone-5-sulphonic acid, which may be neutralized by a metal hydroxide, ammonia solution or an amine.

The examples which follow illustrate the invention without a limitation of the latter being implied.

EXAMPLE 1

A shampoo for protecting the hair is prepared, having the following composition:

| | |
|---|---|
| 2-Hydroxy-4-methoxybenzophenone-5-sulphonic acid sold by the company BASF under the name "UVINUL MS 40" | 1 g |
| Sodium ($C_{12}$–$C_{14}$ alkyl) ether sulphate oxyethylenated with 2.2 moles of ethylene oxide, in aqueous solution containing 25% of active substance (AS) | 6.2 g AS |
| Coconut diethanolamide sold by the company HENKEL under the name "COMPERLAN KD" | 4 g |
| Hydrochloric acid qs pH 5 | |
| Preservative, coloring, perfume qs | |
| Water qs | 100 g |

On bleached hair which has been washed five times using this shampoo and then exposed for 120 hours to the Suntest, a substantial improvement is observed in the mean values of the 15% extension level in the wet state, compared with bleached hair which has undergone a similar treatment but with the shampoo base without "UVINUL MS 40".

The Suntest test is performed using a "SUNTEST HANAU" apparatus, which consists of a xenon emitter and a filter system producing a radiation corresponding to a very large extent to solar radiation. The radiation intensity is approximately 585 W/m$^2$ in the wavelength range between 300 and 830 nm (overall radiation).

EXAMPLE 2

A styling foam for protecting the hair is prepared, having the following composition:

| | |
|---|---|
| Vinyl methyl ether/maleic anhydride copolymer monoesterified with butanol, sold at a concentration of 50% of active substance (AS) in ethanol by the company GENERAL ANILIN under the name "GANTREZ ES 425" | 0.6 g AS |
| Hydroxyethylcellulose grafted with diallyldimethylammonium chloride, sold by the company NATIONAL STARCH under the name "CELQUAT L 200" | 0.5 g |
| Cationic silicone polymer sold by the company UNION CARBIDE under the name "UCAR SILICONE ALE 56" in aqueous solution containing 35% of active substance (AS) | 0.2 g AS |
| 2-Hydroxy-4-methoxybenzophenone-5-sulphonic acid sold by the company BASF under the name "UVINUL MS 40" | 0.5 g |
| Ethyl alcohol qs: 10° strength | |
| 2-Amino-2-methyl-1-propanol qs pH 7.5 | |
| Perfume, coloring, preservative qs | |
| Water qs | 100 g |

The above composition is packaged in an aerosol device:

| | |
|---|---|
| Composition | 90 g |
| Freons 12/114 (57:43 by weight) | 10 g |
| Total | 100 g |

Freon 12 = difluorodichloromethane
Freon 114 = 1,2-dichlorotetrafluoroethane

Permanent-waved natural hair receives an application of this foam and then, without this being followed by a rinse, is subjected to 180 hours' exposure to the Suntest, as described in Example 1.

Compared with hair of the same nature treated in a similar manner but using a foam not containing "UVINUL MS 40", a significant improvement is recorded in the means value of the 15% extension level in the wet state.

EXAMPLE 3

A styling gel for protecting the hair is prepared, having the following composition:

| | |
|---|---|
| 2-Hydroxy-4-methoxybenzophenone-5-sulphonic acid sold by the company BASF under the name "UVINUL MS 40" | 0.3 g |
| Methacrylic acid/methyl methacrylate 50:50 copolymer | 0.8 g AS |
| Hydroxyethylcellulose grafted with diallyldimethylammonium chloride, sold by the company NATIONAL STARCH under the name "CELQUAT L 200" | 0.8 g |
| Cationic silicone polymer sold by the company DOW CORNING under the name "CATIONIC EMULSION DC 929", in aqueous solution containing 35% of active substance (AS) | 0.3 g AS |
| 2-Amino-2-methyl-1-propanol qs pH 7.5 | |
| Ethyl alcohol qs 10° strength | |
| Perfume, coloring, preservative qs | |
| Water qs | 100 g |

Bleached hair is treated with this styling gel in three applications and is then, without being rinsed, subjected to 120 hours' exposure to the Suntest.

Compared with hair of the same nature treated in the same manner but using the said gel without "UVINUL MS 40", a significant improvement is found in the mean value of the 15% extension level in the wet state.

EXAMPLE 4

The styling spray having the following composition is prepared:

| | |
|---|---|
| Crotonic acid/vinyl 4-tert-butylbenzoate/vinyl acetate (10:25:65) terpolymer, prepared according to French Patent No. 2,439,798 (Ex. 19) | 6 g |
| 2-Amino-2-methyl-1-propanol qs for neutralization | |
| 2-Hydroxy-4-methoxybenzophenone-5- | 1 g |

-continued

| | |
|---|---|
| sulphonic acid sold by the company BASF under the name "UVINUL MS 40" Perfume qs | |
| Ethyl alcohol qs | 100 g |

The above composition is packaged in a pump bottle.

One application of this styling spray on bleached hair which is not rinsed and which is then subjected to 120 hours' exposure to the Suntest enables the mean value of the 15% extension level in the wet state to be improved very appreciably, compared with hair of the same nature which has undergone a similar treatment using a spray of identical composition without "UVINUL MS 40".

EXAMPLE 5

A fluid styling gel for protecting the hair is prepared, having the following composition:

| | |
|---|---|
| Crosslinked polyacrylic acid, MW 4,000,000, sold by the company GOODRICH under the name "CARBOPOL 940" | 1 g |
| 2-Hydroxy-4-methoxybenzophenone-5-sulphonic acid sold by the company BASF under the name "UVINUL MS 40" | 0.3 g |
| Diethylenetriaminepentaacetic acid pentasodium salt | 0.2 g |
| Triethanolamine qs pH 7 | |
| Perfume, coloring qs | |
| Water qs | 100 g |

As in Example 3, an improvement is found in the mean value of the 15% extension level in the wet state.

We claim:

1. A process for protecting the elasticity of hair, as measured by its 15% extension level in the wet state, from degradation by light, said process comprising applying to the hair, in an amount effective to protect the elasticity of said hair, a cosmetic composition comprising in a cosmetically acceptable vehicle 0.5 to 9 percent by weight calculated as free acid of 2-hydroxy-4-methoxy-benzophenone-5-sulphonic acid or a salt thereof, said vehicle being an aqueous, alcoholic or an aqueous alcoholic medium, and subsequently rinsing said hair.

2. The process of claim 1 wherein said 2-hydroxy-4-methoxybenzophenone-5-sulphonic acid is salified by a metal hydroxide, an ammonia solution or an amine.

3. The process of claim 1 wherein said cosmetic composition is in the form of a thickened or unthickened aqueous, alcoholic or aqueous-alcoholic solution, a gel, an aerosol foam or a spray.

4. The process of claim 1 wherein said cosmetic composition also includes at least one cosmetic adjuvant selected from the group consisting of a cationic, anionic, amphoteric or nonionic surfactant or a mixture thereof; a thickener; an anionic, nonionic, amphoteric or cationic polymer or a mixture thereof; an emollient; a preservative; a foaming agent; a foam stabilizer; an electrolyte; a pH regulating agent; an antigrease agent; a sequestering agent; a perfume; a coloring agent; a propellant; and an organic solvent.

5. The process of claim 1 wherein said 2-hydroxy-4-methoxybenzophenone-5-sulphonic acid or a salt thereof is present in said cosmetic composition in an amount ranging from 0.5 to 6 percent by weight calculated as free acid based on the total weight of said composition.

6. The process of claim 1 wherein said cosmetic composition is in the form of a shampoo, said composition also including at least one anionic, cationic or amphoteric surfactant, or a mixture thereof, said surfactant being present in an amount ranging from 2 to 50 percent by weight and said vehicle being an aqueous medium.

7. The process of claim 1 wherein said cosmetic composition is in the form of a foam and said vehicle is an aqueous or an aqueous-alcoholic medium, said cosmetic composition also containing a propellant and a foaming agent selected from the group consisting of (1) an anionic, nonionic, cationic or amphoteric surfactant, or a mixture thereof; (2) a nonionic, anionic or cationic polymer, or a mixture thereof; and (3) a polyvinyl alcohol derived from hydrolyzed polyvinyl acetate wherein the degree of hydrolysis is not more than 97%.

8. The process of claim 7 wherein said foaming agent is a combination of a cationic polymer and an anionic polymer, at least one of the said polymers being foaming in water, in the presence of said propellant.

9. The process of claim 1 wherein said cosmetic composition is in the form of a spray or lacquer and said vehicle is an alcoholic or aqueous-alcoholic medium, said cosmetic composition also containing a film-forming resin, said filmforming resin being an anionic polymer containing units of (1) acrylic or methacrylic acid, (2) crotonic acid or (3) an unsaturated $\alpha, \beta$-dicarboxylic acid.

10. The process of claim 9 wherein said cosmetic composition also includes a propellant.

11. A process for protecting the elasticity of hair, as measured by its 15% extension level in the wet state, against degradation by light, said process comprising applying on the hair at least 30 mg/g of hair of a cosmetic composition comprising in a cosmetically acceptable vehicle 0.5 to 9 percent by weight calculated as free acid of 2-hydroxy-4-methoxybenzophenone-5-sulphonic acid or a salt thereof, said vehicle being an aqueous, alcoholic or aqueous-alcoholic medium, and subsequently rinsing said hair.

12. The process of claim 11 wherein said 2-hydroxy-4-methoxybenzophenone-5-sulphonic acid is salified by a metal hydroxide, an ammonia solution or an amine.

13. The process of claim 11 wherein said cosmetic composition is in the form of a thickened or unthickened aqueous, alcoholic or aqueous-alcoholic solution, a gel, an aerosol foam or a spray, said cosmetic composition also containing at least one cosmetic adjuvant selected from the group consisting of a cationic, anionic, amphoteric or nonionic surfactant or a mixture thereof; a thickener; an anionic, nonionic, amphoteric or cationic polymer or a mixture thereof; an emollient; a preservative; a foaming agent; a foam stabilizer; an electrolyte; a pH regulating agent; an anti-perspirant; a sequestering agent; a perfume; a coloring agent; a propellant; and an organic solvent.

14. The process of claim 11 wherein said 2-hydroxy-4-methoxybenzophenone-5-sulphonic acid or a salt thereof is present in said cosmetic composition in an amount ranging from 0.5 to 6 percent by weight calculated as free acid based on the total weight of said composition.

* * * * *